(12) United States Patent
Brock-Fisher

(10) Patent No.: US 6,638,230 B2
(45) Date of Patent: Oct. 28, 2003

(54) APPARATUS AND METHOD OF FREQUENCY COMPOUNDING TO PERFORM CONTRAST IMAGING

(75) Inventor: George A. Brock-Fisher, Andover, MA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 20 days.

(21) Appl. No.: 09/917,949

(22) Filed: Jul. 31, 2001

(65) Prior Publication Data

US 2003/0028098 A1 Feb. 6, 2003

(51) Int. Cl.[7] .................................................. A61B 8/14
(52) U.S. Cl. ........................ 600/458; 600/437; 600/443
(58) Field of Search ................................ 600/437, 441, 600/447, 458, 459

(56) References Cited

U.S. PATENT DOCUMENTS

| | | | | |
|---|---|---|---|---|
| 4,561,019 A | * | 12/1985 | Lizzi et al. | ................. 348/163 |
| 5,196,183 A | * | 3/1993 | Yudelson et al. | ............ 424/9.5 |
| RE35,148 E | * | 1/1996 | Lizzi et al. | ................. 348/163 |
| 5,827,204 A | * | 10/1998 | Grandia et al. | ................. 601/2 |
| 5,879,303 A | * | 3/1999 | Averkiou et al. | ........... 600/447 |
| 5,957,852 A | * | 9/1999 | Hossack et al. | ............ 600/477 |
| 6,102,858 A | * | 8/2000 | Hatfield et al. | ............. 600/443 |
| 6,132,377 A | * | 10/2000 | Bolorforosh et al. | ....... 600/458 |
| 6,139,501 A | | 10/2000 | Roundhill et al. | |
| 6,155,981 A | * | 12/2000 | Ermert et al. | ............... 600/453 |
| 6,179,781 B1 | | 1/2001 | Phillips | |

FOREIGN PATENT DOCUMENTS

WO 96/13213 5/1996

* cited by examiner

Primary Examiner—Francis J. Jaworski
Assistant Examiner—William C. Jung
(74) Attorney, Agent, or Firm—John Vodopia

(57) ABSTRACT

An apparatus and method of imaging contrast agents within a patient's body. The apparatus includes an imaging system transmitting at multiple frequencies to elicit a response from the contrast agent at corresponding multiple frequencies, forms images corresponding to each frequency, and the combines the formed images.

27 Claims, 3 Drawing Sheets

APPARATUS AND METHOD OF FREQUENCY COMPOUNDING TO PERFORM CONTRAST IMAGING

BACKGROUND OF THE INVENTION

1. Field of the Invention

The present invention relates to frequency compounding, and more particularly, to an apparatus and method of frequency compounding to perform contrast imaging using ultrasound to enhance the sensitivity to contrast agents having different sized microbubbles.

2. Description of the Related Art

The use of ultrasound imaging has grown quickly due to the image quality achievable, its safety, and its low cost. Such imaging can be broken into two general categories: tissue imaging and contrast imaging. In contrast imaging, contrast agents, for example microbubbles of heavy gas encapsulated in rupturable shells of material, are introduced intravenously into the bloodstream. Due to their physical characteristics, contrast agents stand out in ultrasound examinations and therefore can be used as markers that identify the amount of blood flowing to or through the observed tissue. In particular, the contrast agents resonate in the presence of ultrasonic fields producing radial oscillations that can be easily detected and imaged. Normally, this response is imaged at the second harmonic of the transmit frequency $f_o$.

Recently, it has been determined that tissue also produces harmonic responses which influence the images produced during contrast imaging. Several techniques have been developed which take advantage of the primarily linear response behavior of tissue to cancel or attenuate the linear tissue signals. In several of these techniques, multiple transmit lines are fired along the same line of sight into the body. The transmit waveform is modified (e.g., in terms of power, phase, or polarity) from line to line to produce a variation in the response received by the transducer. These data points are then processed to remove the influence of their linear components to yield data that primarily contains the non-linear response of the contrast agents.

Although the above-described techniques work well in removing the influence of stationary tissue, there are some more interesting non-linear effects that occur. For example, what makes a microbubble that is, e.g., four microns in diameter, able to be seen with ultrasound is that it resonates and when the ultrasound hits the microbubble, the microbubble expands and contracts and actually rings like a bell and emits a strong enough ultrasound signal back so as to be detected. Most of the contrast agents that are being developed by drug companies presently have microbubbles of widely varying diameters. Their sizes are not well controlled. Some of the drug companies are able to control the diameter very well, but most of them are not, and typically the range of microbubble sizes would be from below one micron up to 20 microns ($\mu$m) or more. The bigger microbubbles, bigger than seven microns ($\mu$m) in an intravenous injection, will get filtered out by the lungs. They will get stuck in the lungs and then metabolize so that there remains a range of microbubbles from seven to sub micron size. The size of a microbubble corresponds to the frequency at which it resonates.

Smaller microbubbles resonate at higher frequencies and bigger microbubbles resonate at lower frequencies. Microbubbles have a fairly high Q, which means that they are fairly selective at how much they resonate with respect to their natural frequency. If a certain microbubble that wants to resonate at one frequency is hit with an ultrasound with another frequency, the microbubble will not resonate nearly as much as it does when hit with its favorite frequency, more or less. Thus, if imaging is performed using a certain frequency, it is possible to really only be able to excite maximally the population of microbubbles which have the size that corresponds to that frequency.

From the above, it can be appreciated that it would be desirable to develop an apparatus and method of contrast imaging in which the response to microbubbles of varying sizes is maximized so as to enhance the imaging sensitivity of the contrast agents.

SUMMARY OF THE INVENTION

The present invention relates to an apparatus and method of imaging contrast agents within a patient's body. The apparatus produces an image of a body part into which a contrast agent has been introduced. The apparatus comprises an imaging system transmitting at multiple frequencies to elicit a response from the contrast agent at corresponding multiple frequencies, forms images corresponding to each frequency, and then combines the formed images.

The method comprises transmitting transmit signals at multiple frequencies to elicit a response from the contrast agent at corresponding multiple frequencies, receiving the transmit signals reflected off the contrast agent, forming images corresponding to each frequency, and combining the formed images.

BRIEF DESCRIPTION OF THE DRAWINGS

The invention can be better understood with reference to the following drawings. The components in the drawings are not necessarily to scale, emphasis instead being placed upon clearly illustrating the principles of the present invention.

DETAILED DESCRIPTION OF THE PREFERRED EMBODIMENTS

The present invention generally relates to contrast imaging. According to one aspect of the invention, contrast agent detection techniques are used to image contrast agent concentrations in certain areas of human tissue. In another aspect of the invention, these techniques are used to measure the direction and velocity of contrast agent flow through the bloodstream. In either case, however, frequency compounding is used to detect microbubbles having varying sizes of the contrast agent to maximize the detection of all the microbubbles of the contrast agent present. Due to the frequency compounding, the contrast agent can be more easily and more clearly imaged.

Figure 1:
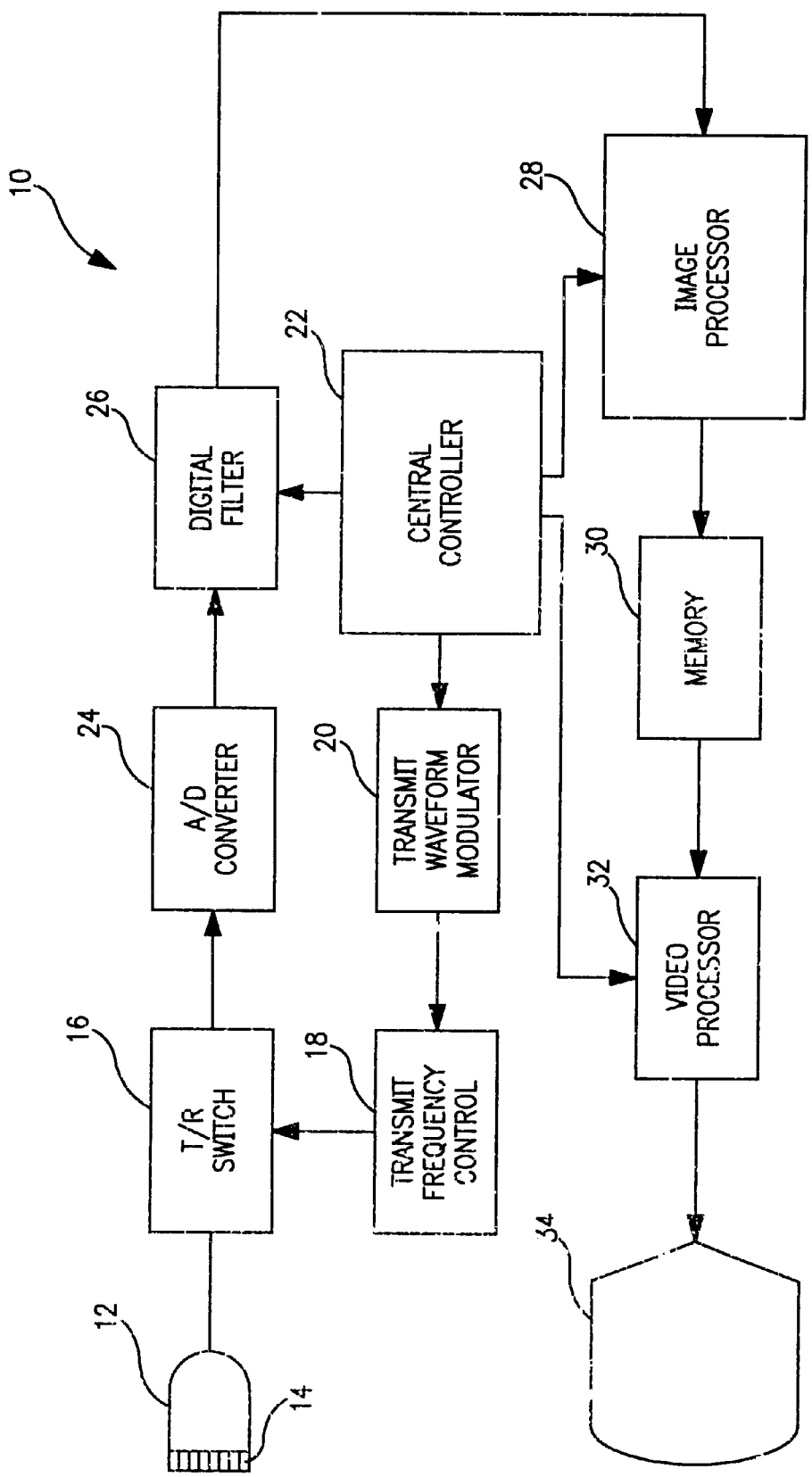
FIG. 1 is a block diagram of a contrast imaging system of the present invention.

Referring now in more detail to the drawings, in which like numerals indicate corresponding parts throughout the several views, FIG. 1 illustrates a contrast imaging system 10 of the present invention. It will be appreciated that this figure does not necessarily illustrate every component of the system, emphasis instead being placed upon the components most relevant to the methods disclosed herein. As indicated in FIG. 1, the system 10 comprises a probe 12 that includes an array transducer 14 that is used to transmit and receive signals. The probe 12 is electrically connected to a T/R switch 16 which places the probe 12 in a transmit or receive mode. On the transmit side, the system 10 includes a transmit frequency control 18 and a transmit waveform modulator 20 that, under the control of a central controller 22, sets the transmit frequency $f_o$ of the transmit signals and modulates the various transmitted signal lines, respectively.

On the receive side, the system 10 includes an A/D converter 24 which converts the analog signals received from the probe 12 via the T/R switch 16 into digital signals and a digital filter 26 (e.g., an RF filter) that filters signals outside the desired receive band from the received data. In addition, the receive side includes an image processor 28 which processes the output from the digital filter 26. The processed data can be stored in a memory 30 and, after being processed by a video processor 32, displayed on a display device 34.

As will be appreciated by those having ordinary skill in the art, the image processor 28 can be implemented in software, hardware, or a combination thereof. It is to be noted that when implemented in software, the image processor 28 can be stored and transported on any computer readable medium for use by or in connection with an instruction execution system, apparatus, or device, such as a computer-based system, processor containing system, or other system that can fetch the instructions from the instruction execution system, apparatus, or device and execute the instructions.

In the context of this disclosure, a "computer readable medium" can be any means that can contain, store, communicate, propagate, or transport the program for use by or in connection with the instruction execution system, apparatus, or device. The computer readable medium can be, for example, an electronic, magnetic, optical, electromagnetic, infrared, or semiconductor system, apparatus, device, or propagation medium. More specific examples of computer readable media include the following: an electrical connection having one or more wires, computer diskette, random access memory (RAM), read only memory (ROM), erasable programmable read only memory (EPROM or Flash memory), an optical fiber, and a compact disk read only memory (CD ROM). It is to be noted that the computer readable medium can even be paper or another suitable medium upon which the program is printed as the program can be electronically captured, via for instance optical scanning of the paper or other medium, then compiled, interpreted, or otherwise processed in a suitable manner if necessary, and then stored in a computer memory. The central controller 22 may be configured in a similar fashion.

Figure 2:
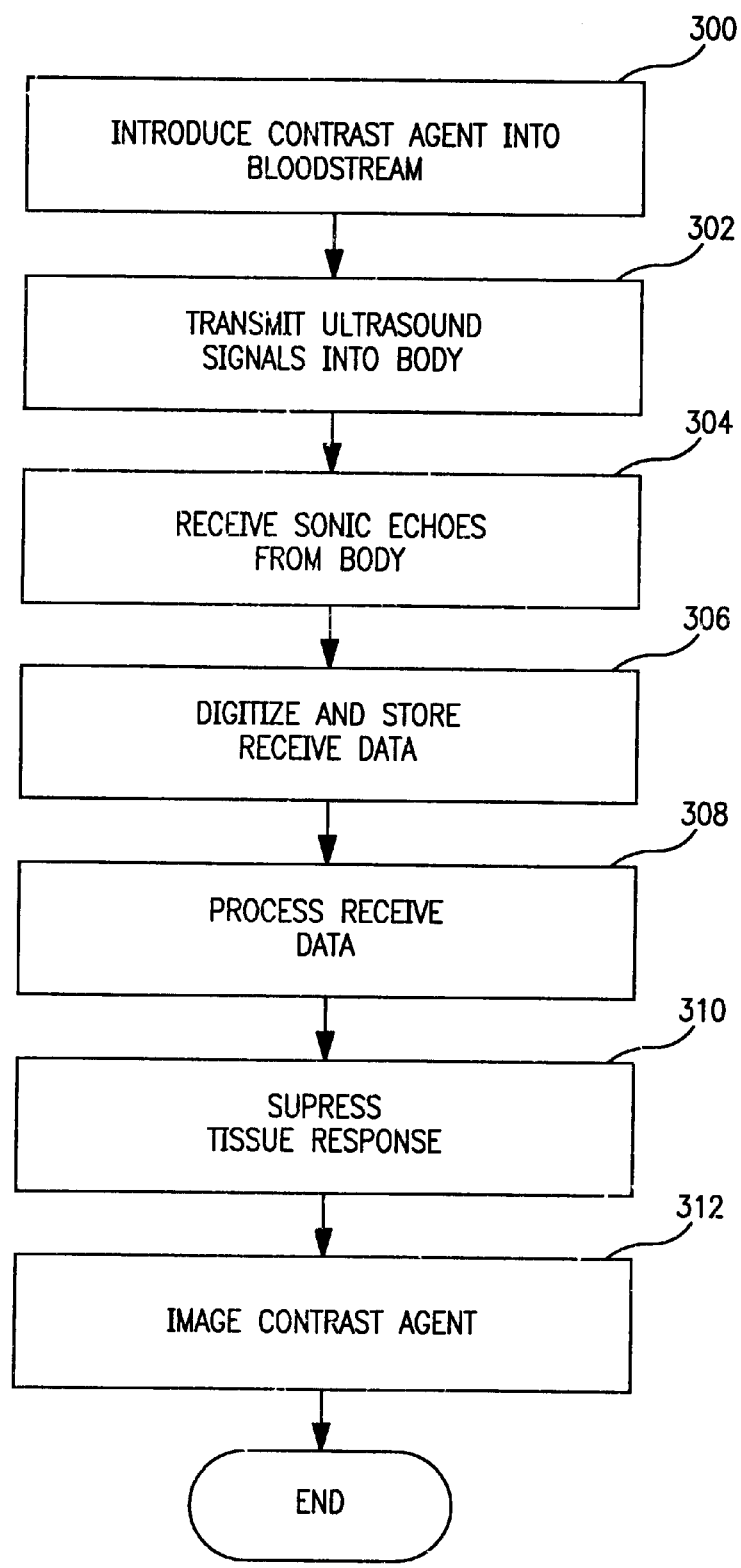
FIG. 2 is a flow diagram of a method of contrast imaging of the present invention.

With reference to FIG. 2, a frequency compounding method of the present invention will be discussed. In particular, FIG. 2 illustrates a high level contrast imaging method and therefore provides a general overview of the inventive method. As indicated in block 300, a contrast agent is first introduced intravenously into the patient's bloodstream. This contrast agent comprises microbubbles of a heavy gas, such as a perfluorocarbon gas encapsulated in an outer shell made of protein, lipid, or other suitable material. Although the size of the agent may vary depending upon the application, these microbubbles normally are in the range of approximately 1.0 to 15 microns ($\mu$m) in diameter. As the contrast agent is introduced into the bloodstream, it travels throughout the cardiovascular system.

After the contrast agent has reached the area to be imaged, ultrasound signals are transmitted into the body, as indicated in block 302. When these acoustic signals intercept the various targets (i.e., tissue and agents) within the body, sonic echoes are produced that are received by the array transducer 14 as indicated in block 304. Additional details regarding the transmit and receive of the ultrasound signals will be provided later on with regard to the discussion of FIG. 3.

Once the acoustic signals have been received from the body, these signals are digitized and stored, as indicated in block 306, so that the data contained therein are processed as indicated in block 308 and ultimately imaged. The linear components of the receive data are removed to suppress the tissue response as indicated in block 310. Thereafter, the contrast agent is imaged using contrast data processing techniques as indicated in block 312. As described below, this imaging can comprise simply imaging the concentration of the contrast agents within human tissue, or can comprise identifying the direction and velocity of flow of contrast agents within the bloodstream or tissues.

A general overview of the imaging method having been provided above, the preferred method will now be discussed in greater detail with reference to FIG. 3.

As noted previously, most of the contrast agents that are being developed by drug companies presently have microbubbles of widely varying diameters. Their sizes are not well controlled. The bigger microbubbles, bigger than seven microns in an intravenous injection, will get filtered out by the lungs. They will get stuck in the lungs and then metabolize so that there remains a range of microbubbles from seven to sub micron size and the size of a microbubble corresponds to the frequency at which it resonates.

Smaller microbubbles resonate at higher frequencies and bigger microbubbles resonate at lower frequencies. Microbubbles have a fairly high Q, which means that they are fairly selective at how much they resonate with respect to their natural frequency. If a certain microbubble that is resonant at one frequency is hit with an ultrasound with another frequency, the microbubble will not resonate nearly as much as it does when hit with its favorite frequency, more or less. Thus, if imaging is performed using a certain frequency, it is possible to really only be able to excite maximally the population of microbubbles which have the size that corresponds to that frequency.

So an idea of this invention is to use frequency compounding where ultrasound signals are transmitted selectively at different frequencies. An ultrasound signal is transmitted at one frequency which might be lower and will be able to pick up signals from the larger microbubbles in the population and then another ultrasound signal at a higher frequency will be transmitted to pick up signals from microbubbles that are smaller. After forming both of those images, the two images are combined together and the result is an image that is sensitive to a greater number of microbubbles than either one of them alone.

Figure 3:
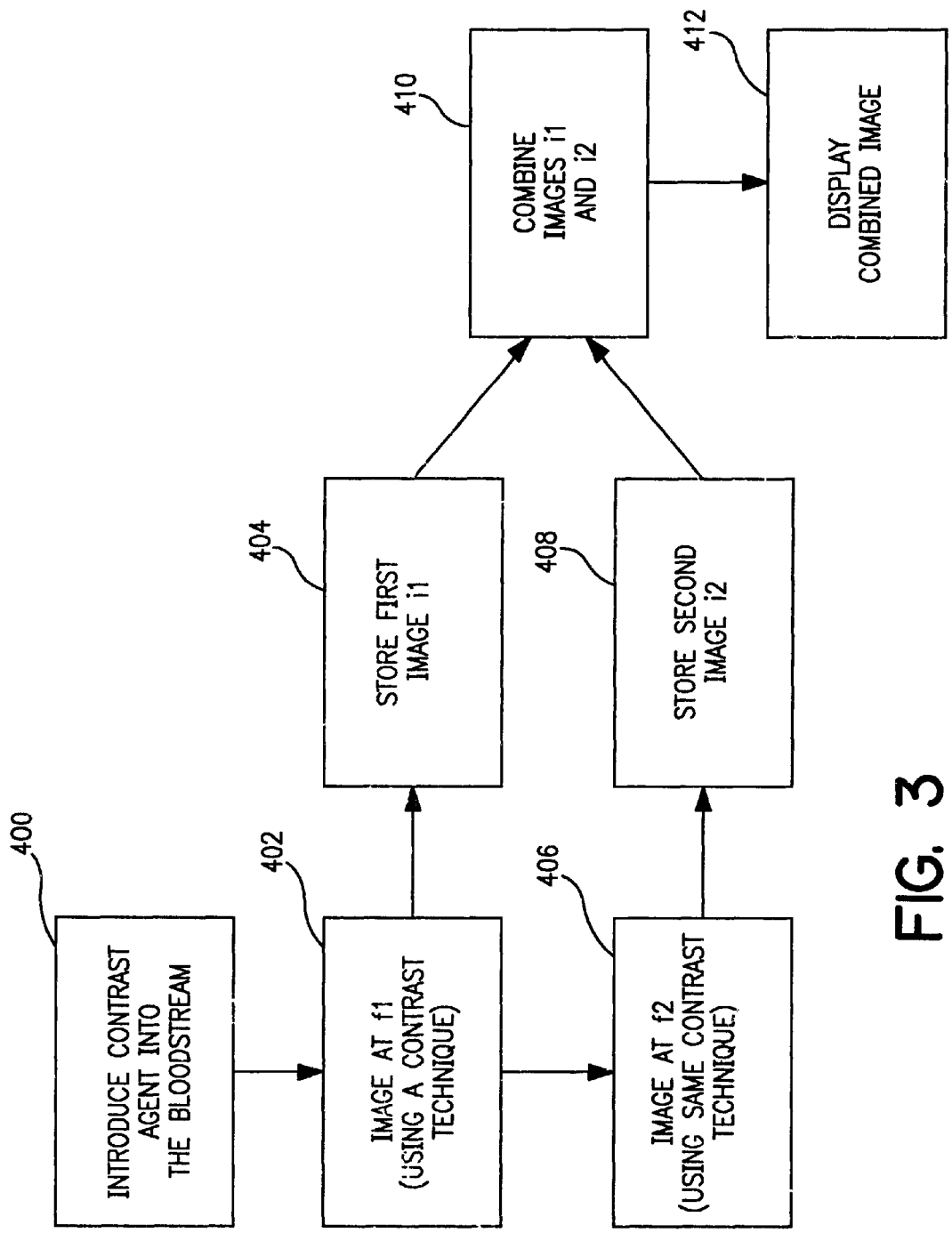
FIG. 3 is a flow diagram of details of the method for contrast imaging of the present invention, shown in FIG. 2.

FIG. 3 shows a contrast agent is administered to a patient, as indicated in block 400, in a manner as described above. Then, the central controller 22 causes the array transducer 14, through the transmit waveform modulator 20, the transmit frequency control 18 and the T/R switch 16, to image at a first frequency f1 as indicated in block 402 using any contrast technique as discussed below and store an image i1 in the memory 30 as indicated in block 404. The central controller 22 causes the array transducer 14 to image at a second frequency f2 different from the first frequency f1 as indicated in block 406 and use the contrast technique as before with regard to the first frequency f1. An image i2 is stored in the memory 30 as indicated in block 408. The first image i1 and the second image i2 are combined as indicated in block 410 and then displayed as indicated in block 412. It is important thing to note that these operations can be done in any order. The operations could be by the frame, where a whole frame is imaged at the first frequency f1 and then a whole frame is imaged at the second frequency. However, the imaging may be performed line to line because it is advantageous to make the second image i2 as quickly as possible after the first image i1 so that motion does not substantially affect the images i1 and i2.

The combination in block 410 encompasses either a coherent combination or an incoherent combination.

There have been developed a number of different contrast techniques as briefly mentioned above, for suppressing linear tissue response and thus optimizing microbubble detection. In the present invention, the frequency compounding may be added to any one of these contrast techniques to achieve an image which is sensitive to a greater number of microbubbles than either the frequency compounding or the contrast technique alone.

The contrast techniques include power modulation, phase modulation, pulse inversion, coded pulse sequence modulation, and second harmonic imaging. With the exception of the second harmonic imaging, each of these techniques basically starts off with sending multiple transmits at the microbubbles and modifying the transmit in a particular manner, perhaps by changing the power, the phase, the polarity, the pulse probe sequence modulation, etc. Then on receive, processing is performed on the received data to invert the modification. Thus, each of these contrast techniques involves doing a reciprocal operation on receive from the one done on transmit with the desired result of being able to cancel linear tissue signals and increasing the ratio of signals from microbubbles to signals from tissue.

In a first modulation technique, the power modulation technique, the amplitude of the transmit signals is varied from transmit line to transmit line to provide power modulation of the transmit signals. For instance, if five separate lines are fired along the same line of sight, the amplitudes of the various lines can be scaled such that the first, third, and fifth lines have an amplitude that is half that of the second and fourth transmitted lines (i.e., 0.5, 1.0, 0.5, 1.0, 0.5). Due to the linear response characteristics of tissue, the tissue response to the half-amplitude transmit signals will be half the magnitude of that of the tissue response to the full amplitude transmit signals. A gain factor is then applied to the receive data to account for the unequal transmitted amplitudes. For instance, in the transmission scheme described above, the first, third and fifth line responses are multiplied by a factor of two. When this is done, the response signals of the various transmit lines are subtracted from each other to cancel all linear components of the signals. Due to the non-linear response of the microbubbles of the contrast agent, however, this subtraction does not cancel contrast agent signals. Accordingly, through this technique, the tissue signals are suppressed to improve the signal-to-noise ratio of the data. For a detailed example of power modulation of transmit signals, reference is made to U.S. Pat. No. 5,577,505, issued to Brock-Fisher, et al, commonly assigned with the present application, and which is hereby incorporated by reference into the present disclosure.

In the power modulation technique, ultrasonic energy is steered in a certain direction and signals are received that are reflected back on a body and the signals are accumulated. By virtue of focusing on receive, the probe 12 may only be sensitive to signals that come from the same direction and therefore, angles with respect to the array transducer 14 are known. The distance from the array transducer 14 is determined by virtue of how much time it took for the signal to propagate and come back. In the power modulation technique, the array transducer 14 shoots a transmit signal at a certain angle and receives back from that angle and stores that data in the memory 102 and then the transducer 14 shoots a signal at the same angle but with a different power level. Assuming that the second power level is twice the first power level, the array transducer 14 receives back the signals from that angle and stores that in a memory. The image processor 28 applies a received gain compensation factor to one of the two lines so that the two lines have the same net gain. For example, a gain of one-half could be applied to the line that was transmitted with an intensity of twice the other and then one of the two lines is subtracted from the other one.

When inspecting a linear target, when the double size signal is received from the double size transmit and multiplied by half, the previous double size signal looks the same as the signal from the regular, the first transmit. Upon subtraction, nothing is left. What this technique does, it suppresses the reflections, the signals from tissue, from linear signals. At the same time, if there is a microbubble out there, then on the line where the power is doubled, the microbubble expands and contracts much further and provides a signal that is much more than twice as big as the first one. When compensation and subtraction are performed, there is still a signal left over. By doing this power modulation processing, a contrast technique is performed where the signals from tissue are separated away from the signals from microbubbles. In its most basic sense, such a contrast technique requires two lines to be transmitted at the same angle at two different power levels.

By shooting one line with low power and another one with high power, then on receive, the gain on the high power line is reduced so as to match the low power line. Then the two lines are subtracted and a comparison is performed. What happens is that tissue which is primarily linear is subtracted out once this compensation is performed. The microbubbles which are not linear remain in the signal.

In adding the frequency compounding on top of the contrast technique such as power modulation, instead of shooting two lines to do a power modulation sequence having a certain frequency, the central controller 22 causes the array transducer 14 to shoot two lines at the first frequency f1 at different power levels. On receive, one of these two lines is multiplied in the image processor 28 by a gain factor inversely proportional to a relative ratio of the power level of the second line relative to the power level relative to the first line. The two lines, after the application of the gain factor to one of the lines, are combined to form a first power modulation image. Then another two lines are shot in the same direction at the second frequency f1. Similarly, on receive, one of these two lines is multiplied by the gain factor. The two lines, after application of the gain factor to one of the lines, are combined to form a second power modulation image which is sensitive to different sized microbubbles from the first power modulation image is formed. The first and second power modulation images are added together to increase the sensitivity to a greater number of microbubbles.

Thus, if there was a microbubble that was missed at the first frequency f1 because it was not of the proper size to respond to the first frequency, the microbubble will hopefully be picked up with the second frequency f2, thereby making the system more sensitive to more different sized microbubbles than if the frequency compounding were not employed.

Because frequency is orthogonal from the modification done in the power modulation, as well as the other contrast techniques, the frequency compounding may be applied to the other contrast techniques as well without affecting their basic operation.

For example, in a second modulation technique, a phase modulation technique, the various transmit signals can be phase modulated. With this technique, the carrier phase of the transmit signals is varied from line to line. By way of example, the phase of the transmit waveform can be incrementally altered by 90° line by line. As with the power modulation technique, the phase modulation produces variations in the response signals received from the body. The linear components of these response signals will be phase shifted to the same degree as the transmit signals from which they were created. Accordingly, if the receive data is phase adjusted to account for these phase shifts, the linear components of the response data can again be cancelled to suppress the tissue response. For detailed examples of phase modulation, reference is made to U.S. Pat. No. 5,632,277, issued to Chapman, et al. and U.S. Pat. No. 5,902,243, issued to Holley, et al, each of which is hereby incorporated by reference into the present disclosure.

In adding the frequency compounding on top of the contrast technique such as phase modulation, instead of shooting two lines to do a phase modulation sequence having a certain frequency, now the array transducer 14 shoots two lines at the first frequency f1 at different phases. One of these two lines is filtered to compensate for the different phases on receive. The two lines, after the filtering of one of the lines, are combined to form a first phase modulation image. Then another two lines are shot in the same direction at the second frequency f1. Similarly, on receive, one of these two lines is filtered to compensate for the different phases. The two lines, after application of the filtering to one of the lines, are combined to form a second phase modulation image, which is sensitive to different sized microbubbles from the first power modulation image. The first and second phase modulation images are combined together to increase the sensitivity to a greater number of microbubbles.

In a third modulation technique, a pulse inversion technique, the polarity of the transmit signals is varied. For instance, the various transmit lines have alternating positive and negative polarities. Again, once the data received from these transmit lines are corrected to account for the variations in the transmit signals, the linear components of the received data are cancelled to attenuate the response of the tissue. For a detailed example of polarity modulation, reference is made to U.S. Pat. No. 5,706,819, issued to Huang, et al., which is hereby incorporated by reference into the present disclosure.

The way pulse inversion works is the array transducer 14 shoots two lines along a specific direction and shoots one with a certain polarity and a second one with the opposite polarity. Consequently because the inversion was already done on the transmit, there is no need to perform a subtraction, as the images from the two lines are just added together. If the same reflector is out there both times, it will cancel and add to zero. If there is something non-linear out there like a microbubble, then the response will be added upon receive and there will be a signal present.

When adding the frequency compounding to the pulse inversion technique, instead of two lines being shot, the array transducer 14 shoots four lines, with the first two lines being transmitted at the first frequency f1 to produce the first image i1 and the second two lines being transmitted at the second frequency f2 to produce the second image i2. Then, the first and second images I1, I2 are simply added together.

According to a fourth contrast technique, coded pulse sequence modulation, coded sequences are generated where the first transmit event is a sequence of pulses and the second transmit event is a different sequence of pulses. Then on receive, the sequence of pulses of one of the first and second transmit events is passed through a filter which essentially does a transformation from one sequence to the other. Then, one of the filtered sequence and the unfiltered sequence is subtracted from the other in a similar fashion as in the previous contrast techniques.

When adding frequency coding to the coded pulse sequence contrast technique, the first and second transmit events are shot at the first frequency f1. On receive, one of these first and second transmit events are filtered to transform the code pulse sequence to that of the other transmit event. The two lines, after the filtering to one of the lines, are combined to form a first coded pulse sequence image. Then, the first and second transmit events are shot in the same direction at the second frequency f2. On receive, one of these first and second transmit events is filtered to transform the code pulse sequence to that of the other transmit event. The two lines, after the filtering to one of the lines, are combined to form a second coded pulse sequence image. The first and second coded pulse sequence images are added together to increase the sensitivity to a greater number of microbubbles.

According to a fifth modulation technique, a second harmonic technique, where contrast agents are to be imaged, echoes may be received at the second harmonic of the transmit signals. Accordingly, the receive frequency typically will be twice that of the transmit frequency $f_o$. Reception of signals at the second harmonic is advantageous in that contrast agents resonate at this frequency to a much greater extent than does human tissue. Accordingly, the response of the contrast agents can be differentiated from human tissue. Despite this difference in response characteristics, human tissue does produce harmonic responses. Accordingly, the signals received from the body of the patient will normally comprise both contrast image components and tissue components.

In second harmonic imaging, the array transducer 14 essentially transmits at a certain frequency but on receive, instead of tuning receive filters around the transmitted frequency, the receive filters are tuned around the second harmonic of the transmitted frequency. When the microbubbles resonate, the signals they give out contain a lot of second harmonic content and at the same time, the signals that tissue gives out contain some second harmonic content but less. As a result, it is possible to get a little bit more differentiation between contrast agent and tissue.

When adding the frequency compounding to the second harmonic imaging contrast technique, the array transducer 14 transmits at a first frequency and receives at another frequency, e.g., twice the frequency, to form a first second harmonic image. Then, the array transducer 14 transmits at a second frequency and receives at another frequency, e.g., twice the second frequency, to form a second second harmonic image. Then, the first and second second harmonic images are combined.

The present invention is not and should not be limited to transmitting two lines. All of the contrast techniques may be expanded to more than two lines. Certainly, instead of transmitting at two power levels, three power levels may be transmitted. Also, a line at one power level, a second line at a second power level, and then a third line at the first power level may be transmitted. Still further, the number of frequencies is not limited to two frequencies. Additional frequencies may be used in conjunction with any of the contrast techniques discussed above. Thus, the number of lines may changed according to different embodiments. Essentially, whichever a contrast technique is used, the contrast technique will be repeated at different transmit frequencies to try to pick up sensitivity from different sized microbubbles. In employing these contrast techniques, multiple lines are shot and a characteristic of the transmit signal is altered for at least one of the lines. On receive, the change in characteristic is reversed, except when employing the second harmonic imaging. After undoing whatever changes were made, a subtraction is performed between the two images formed.

Irrespective of the particular transmit signal modulation technique used, each transmit line normally comprises repeated sequences of waveforms. By way of example, each waveform comprises a Gaussian-modified sinusoid. The various transmit lines are fired along the same line of sight into the body. Each group of lines fired in this direction is referred to as a packet of lines. Normally, specific sequences of transmit waveforms are used and repeated multiple times within each packet. Each sequence of transmit waveforms is referred to as a sub-packet.

After the multiple lines have been transmitted into the body, the response echoes are received. Again, these received signals are digitized, so that the data contained therein is processed in the appropriate manner. Once digitized, these received data are stored in memory. The various data can be processed to remove the linear components of the data that pertain to tissue. This normally comprises subtracting the various lines of data from each other with a contrast imaging clutter filter to cancel the linear components. By way of example, the data of a first column (line 1) can be subtracted from that of a second column (line 2) to filter the linear components portion of the signal, so that only non-linear components remain. Once the linear components of the signal have been removed in this manner, the data can be processed to image the contrast agent. In one embodiment, this imaging comprises contrast agent concentration imaging according to known techniques. In another embodiment, techniques similar to those used color flow imaging are used to image the direction and velocity of travel of the contrast agents within the bloodstream. In either case, however, advantageous results are obtained due to the maximization of detection of the microbubbles having different sizes of the contrast agent through the use of frequency compounding.

The frequency compounding technique of the present invention is usable with a linear array. The present invention would also be useful on a two-dimensional (2D) array that is used to produce a three-dimensional (3D) picture. The present invention may be usable in a 3D imaging system. In addition, the present invention is usable on the transmit because it has a mechanically movable element. In some ultrasound systems, the transducer is mechanically steered. In this type of ultrasound system, the transducer is packaged inside of a lens with some oil so as to be able to move freely, while transmitting in various directions.

Consequently, by using frequency compounding in an ultrasound imaging system for producing an image of a body part into which a contrast agent has been introduced, it is possible to maximize detection of microbubbles of different sizes of the contrast agent. Further, by combining the frequency compounding with various contrast techniques, it is possible to separate contrast agent response, which is non-linear, from tissue response which is linear.

While particular embodiments of the invention have been disclosed in detail in the foregoing description and drawings for purposes of example, it will be understood by those skilled in the art that variations and modifications thereof can be made without departing from the scope of the invention as set forth in the following claims.

The many features and advantages of the invention are apparent from the detailed specification and, thus, it is intended by the appended claims to cover all such features and advantages of the invention that fall within the true spirit and scope of the invention. Further, since numerous modifications and changes will readily occur to those skilled in the art, it is not desired to limit the invention to the exact construction and operation illustrated and described, and accordingly all suitable modifications and equivalents may be resorted to, falling within the scope of the invention.

What is claimed is:

1. An ultrasound imaging system that produces an image of a body part into which contrast agent microbubbles of varying sizes have been introduced, wherein each size of microbubble has a corresponding resonant frequency, the device comprising:

a means for transmitting signals at different frequencies, wherein, for each particular one of the different transmitted frequencies, microbubbles of a size having a corresponding resonant frequency closest to the particular transmitted frequency have the greatest response;

a means for receiving echo signals corresponding to each transmitted frequency; and a means for combining the received echo signals to form a display image.

2. The ultrasound imaging system as claimed in claim 1, wherein the means for combining the received echo signals forms one of a coherent combination containing phase information and an incoherent combination not containing phase information.

3. The ultrasound imaging system as claimed in claim 1, wherein the ultrasound imaging system performs at least one of the following modulation techniques: power modulation, phase modulation, pulse inversion, coded pulse sequence modulation, and harmonic imaging.

4. The ultrasound imaging system as claimed in claim 1, wherein the ultrasound imaging system performs a power modulation technique in which:

the means for transmitting signals generates a first plurality of transmit signals having at least two different power levels at a first frequency, and generates a second plurality of transmit signals having the at least two different power levels at a second frequency different from the first frequency;

the means for receiving echo signals receives echo signals of the first and second pluralities of transmit signals; and the means for combining the received echo signals applies at least one gain compensation factor to the echo signals to achieve a substantially similar power level for all the echo signals, combines the gain compensated echo signals corresponding to the first plurality of transmit signals to generate a first image, combines the gain compensated echo signals corresponding to the second plurality of transmit signals to generate a second image, and combines the first and second images to generate the display image.

5. The ultrasound imaging system as claimed in claim 4, wherein the at least two different power levels comprise a first power level and a second power level which is twice the first power level, and the gain compensation factor of 0.5 is applied to the echo signals corresponding to the transmit signals transmitted at the second power level.

6. The ultrasound imaging system as claimed in claim 4, wherein the at least two different power levels comprise a first power level and a second power level which is twice the first power level, wherein each of the first and second pluralities of transmit signals comprises a series of signals transmitted at the first power, the second power level and then the first power level in order, and the gain compensation factor of 0.5 is applied to the echo signals corresponding to the transmit signals transmitted at the second power level.

7. The ultrasound imaging system as claimed in claim 1, wherein the ultrasound imaging system performs a phase modulation technique in which:
the means for transmitting signals generates a first plurality of transmit signals having at least two different phases at a first frequency, and generates a second plurality of transmit signals having the at least two different phases at a second frequency different from the first frequency;
the means for receiving echo signals receives echo signals of the first and second pluralities of transmit signals; and
the means for combining the received echo signals applies at least one phase compensation factor to the echo signals to achieve a substantially similar phase for all the echo signals, combines the phase compensated echo signals corresponding to the first plurality of transmit signals to generate a first image, combines the phase compensated echo signals corresponding to the second plurality of transmit signals to generate a second image, and combines the first and second images to generate the display image.

8. The ultrasound imaging system as claimed in claim 1, wherein the ultrasound imaging system performs a pulse inversion modulation technique in which:
the means for transmitting signals generates a first plurality of transmit signals having first and second polarities at a first frequency, and generates a second plurality of transmit signals having the first and second polarities at a second frequency different from the first frequency;
the means for receiving echo signals receives echo signals of the first and second pluralities of transmit signals; and
the means for combining the received echo signals combines the echo signals of the first plurality of transmit signals to generate a first image, combines the echo signals of the second plurality of transmit signals to generate a second image, and combines the first and second images to generate the display image.

9. The ultrasound imaging system as claimed in claim 1, wherein the ultrasound imaging system performs a coded pulse sequence modulation technique in which:
the means for transmitting signals generates a first plurality of transmit signals having a first pulse code sequence at a first frequency, and generates a second plurality of transmit signals having a second pulse code sequence at a second frequency different from the first frequency;
the means for receiving echo signals receives echo signals of the first and second pluralities of transmit signals;

the means for combining received echo signals filters echo signals of one of the first and second pluralities of transmit signals to transform the corresponding pulse code sequence to the other pulse code sequence, combines the filtered echo signals to form a first image, combines the other echo signals to form a second image, and combines the first and second images to generate the display image.

10. The ultrasound imaging system as claimed in claim 1, wherein the ultrasound imaging system performs a harmonic imaging technique in which:
the means for transmitting signals generates a first plurality of transmit signals at a first frequency;
the means for receiving echo signals receives a first plurality of echo signals corresponding to the first plurality of transmit signals and tuned around a second frequency different from the first frequency;
the means for transmitting signals generates a second plurality of transmit signals at a third frequency;
the means for receiving echo signals receives a second plurality of echo signals corresponding to the second plurality of transmit signals and tuned around a fourth frequency different from the third frequency; and
the means for combining the received echo signals combines the first and second plurality of echo signals to generate the image.

11. The ultrasound imaging system as claimed in claim 10, wherein the second frequency is a harmonic of the first frequency and the fourth frequency is a harmonic of the third frequency.

12. The ultrasound imaging system as claimed in claim 1, wherein the means for transmitting signals comprises at least one of:
a linear array generating acoustic signals at the multiple frequencies; or
a two dimensional array transducer generating acoustic signals at multiple frequencies.

13. The ultrasound imaging system as claimed in claim 1, wherein the means for transmitting signals and the means for receiving echo signals comprise an ultrasonic transducer.

14. The ultrasound imaging system as claimed in claim 1, wherein the ultrasonic imaging system is a three dimensional imaging system.

15. The ultrasound imaging system as claimed in claim 1, wherein the different frequencies comprise a first and a second frequency, a first image is formed from received echo signals of the transmit signals of the first frequency, a second image is formed from received echo signals of the transmit signals of the second frequency, and then the display image is formed by combining the first and second images.

16. The ultrasound imaging system as claimed in claim 1, wherein the different frequencies comprise a first and a second frequency, wherein the display image is comprised of a frame which in turn is comprised of lines which alternate between lines of a first type and lines of a second type, and wherein the lines of a first type are formed from received echo signals of the transmit signals of the first frequency, and the lines of the second type are formed from received echo signals of the transmit signals of the second frequency.

17. A method of producing an image of a body part into which contrast agent microbubbles of varying sizes have been introduced, wherein each size of microbubble has a corresponding resonant frequency, the method comprising:
transmitting transmit signals at different frequencies, wherein, for each particular one of the transmitted frequencies, microbubbles of a size having a corresponding resonant frequency closest to the particular transmitted frequency have the greatest response;

receiving echo signals signals corresponding to each transmitted frequency; and combining the received echo signals to form a display image.

18. The method according to claim 17, wherein the step of transmitting comprises the steps of:

transmitting transmit signals at a first frequency; and transmitting transmit signals at a second frequency.

19. The method according to claim 17, wherein a power modulation technique is used in which:

the step of transmitting comprises the steps of:

generating a first plurality of transmit signals having at least two different power levels at a first frequency, and generating a second plurality of transmit signals having the at least two different power levels at a second frequency different from the first frequency;

the step of receiving comprises the step of:

receiving echo signals of the first and second pluralities of transmit signals; and the step of combining comprises the steps of:

applying at least one gain compensation factor to the echo signals to achieve a substantially similar power level for all the echo signals, combining gain compensated echo signals corresponding to the first plurality of transmit signals to generate a first image, combining gain compensated echo signals corresponding to the second plurality of transmit signals to generate a second image, and combining the first and second images to generate the display image.

20. The method as claimed in claim 19, wherein the at least two different power levels comprise a first power level and a second power level which is twice the first power level, and the step of applying at least one gain compensation factor comprises the step of:

applying a gain compensation factor of 0.5 to the echo signals corresponding to the transmit signals transmitted at the second power level.

21. The method as claimed in claim 19, wherein the at least two different power levels comprise a first power level and a second power level which is twice the first power level, wherein each of the first and second pluralities of transmit signals comprises a series of signals transmitted at the first power, the second power level and then the first power level in order, and the step of applying at least one gain compensation factor comprises the step of:

applying a gain compensation factor of 0.5 to the echo signals corresponding to the transmit signals transmitted at the second power level.

22. The method as claimed in claim 17, wherein a phase modulation technique is used in which:

the step of transmitting comprises the steps of:

generating a first plurality of transmit signals having at least two different phases at a first frequency, and generating a second plurality of transmit signals having the at least two different phases at a second frequency different from the first frequency;

the step of receiving comprises the step of:

receiving echo signals of the first and second pluralities of transmit signals; and the step of combining comprises the steps of:

applying at least one phase compensation factor to the echo signals to achieve a substantially similar phase for all the echo signals, combining the phase compensated echo signals corresponding to the first plurality of transmit signals to generate a first image, combining the phase compensated echo signals corresponding to the second plurality of transmit signals to generate a second image, and combining the first and second images to generate the display image.

23. The method as claimed in claim 17, wherein a phase modulation technique is used in which:

the step of transmitting comprises the steps of:

generating a first plurality of transmit signals having first and second polarities at a first frequency, and generating a second plurality of transmit signals having the first and second polarities at a second frequency different from the first frequency;

the step of receiving comprises the step of:

receiving echo signals of the first and second pluralities of transmit signals; and the step of combining comprises the steps of:

combining the first plurality of transmit signals to generate a first image, combining the second plurality of transmit signals to generate a second image, and combining the first and second images to generate the display image.

24. The method as claimed in claim 17, wherein a pulse inversion modulation technique is used in which:

the step of transmitting comprises the steps of:

generating a first plurality of transmit signals having a first pulse code sequence at a first frequency, and generating a second plurality of transmit signals having a second pulse code sequence at a second frequency different from the first frequency;

the step of receiving comprises the step of:

receiving echo signals of the first and second pluralities of transmit signals;

the step of combining comprises the steps of:

filtering one of the received first and second pluralities of transmit signals to transform the corresponding pulse code sequence to the other pulse code sequence, combining the transformed plurality of reflected signals to form a first image, combining the other plurality of reflected signals to form a second image, and combining the first and second images to generate the image.

25. The method as claimed in claim 17, wherein a harmonic imaging technique is used in which:

the step of transmitting comprises the steps of:

generating a first plurality of transmit signals at a first frequency, and generating a second plurality of transmit signals at a third frequency, the step of receiving comprises the step of:

receiving a first plurality of echo signals corresponding to the first plurality of transmit signals and tuned around a second frequency different from the first frequency, and receiving a second plurality of echo signals corresponding to the second plurality of transmit signals and tuned around a fourth frequency different from the third frequency;

the step of combining comprises the step of:
  combining the first and second pluralities of echo signals to form the display image.

26. The method as claimed in claim 25, wherein the second frequency is a harmonic of the first frequency and the fourth frequency is a harmonic of the third frequency.

27. A computer readable medium configured for performing a method of producing an image of a body part into which contrast agent microbubbles of varying sizes have been introduced, wherein each size of microbubble has a corresponding resonant frequency, the method comprising:

transmitting transmit signals at frequencies, wherein, for each particular one of the transmitted frequencies, microbubbles of a size having a corresponding resonant frequency closest to the particular transmitted frequency have the greatest response;

receiving echo signals signals corresponding to each transmitted frequency; and combining the received echo signals to form a display image.

* * * * *